(12) United States Patent
Marino

(10) Patent No.: US 6,266,394 B1
(45) Date of Patent: *Jul. 24, 2001

(54) IMAGE INTENSIFIER RETICLE SYSTEM

(75) Inventor: James F. Marino, La Jolla, CA (US)

(73) Assignee: NuVasive, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/326,740

(22) Filed: Jun. 4, 1999

Related U.S. Application Data

(60) Provisional application No. 60/088,663, filed on Jun. 9, 1998.

(51) Int. Cl.[7] .................................................... A61B 6/08
(52) U.S. Cl. ............................................. 378/162; 378/205
(58) Field of Search .................................. 378/162, 163, 378/164, 205; 33/645

(56) References Cited

U.S. PATENT DOCUMENTS

| 4,722,336 | 2/1988 | Kim et al. | 128/303 B |
| 5,189,690 | * 2/1993 | Samuel | 378/162 |

* cited by examiner

*Primary Examiner*—David P. Porta
(74) *Attorney, Agent, or Firm*—Townsend and Townsend and Crew LLP

(57) ABSTRACT

A method of aligning a C-arm of an image intensifier for rotation in a selected plane, the C-arm having a transmitter mounted at one end and a receiver mounted at an opposite end, comprising: identifying the selected plane by viewing the location of bony structures with the image intensifier; and aligning indicia disposed on a radio-opaque reticle covering at least a portion of the receiver with the selected plane, the indicia being aligned with the plane of rotation of the C-arm, thereby aligning the plane of the C-arm with the selected plane.

8 Claims, 7 Drawing Sheets

IMAGE INTENSIFIER RETICLE SYSTEM

CROSS-REFERENCES TO RELATED APPLICATIONS

The present application is a regular application claiming benefit under 35 U.S.C. §119(e) from U.S. Provisional patent application Ser. No. U.S. Provisional patent application Ser. No. 60/088,663 filed Jun. 9, 1998. This application is incorporated herein by reference in its entirety for all purposes.

TECHNICAL FIELD

The present invention relates to C-arm surgical image intensifiers.

SUMMARY OF THE INVENTION

The present invention provides a reticle for attachment to an image intensifier and a method of use which allows a standard C-arm image intensifier to be easily aligned to rotate in a selected plane about any desired point in a human body. The present invention can be used to align an image intensifier to rotate in any plane through the human body, wherein the plane is preferably defined by viewing bones or other radio-opaque structures in the body with the image intensifier system. Although the present invention can be aligned to rotate the C-arm in any desired plane passing through a human body, the present invention is ideally suited to align a conventional C-arm image intensifier to rotate in a plane passing between two adjacent vertebrae in a patient's spine. It is to be understood, however, that the present invention is not so limited to alignment of C-arm image intensifiers only with respect to intervertebral planes.

After aligning the orientation of the image intensifier with the selected intervertebral plane, the image intensifier can be rotated about a selected point to provide both lateral and anterior-posterior views through the patient while remaining in the selected intervertebral plane.

DESCRIPTION OF THE SPECIFIC EMBODIMENTS

Figure 1:
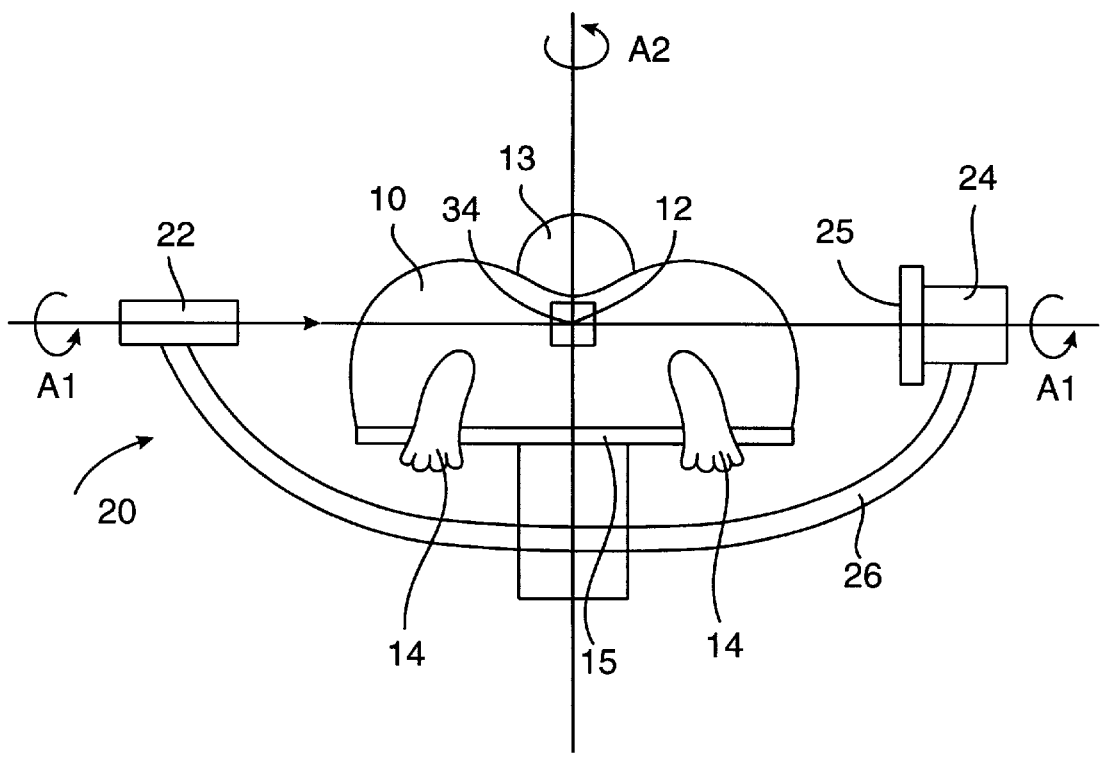
FIG. 1 is a rear elevation view of a prone lying patient with image intensifier taking a lateral view through the patient.
Figure 2:
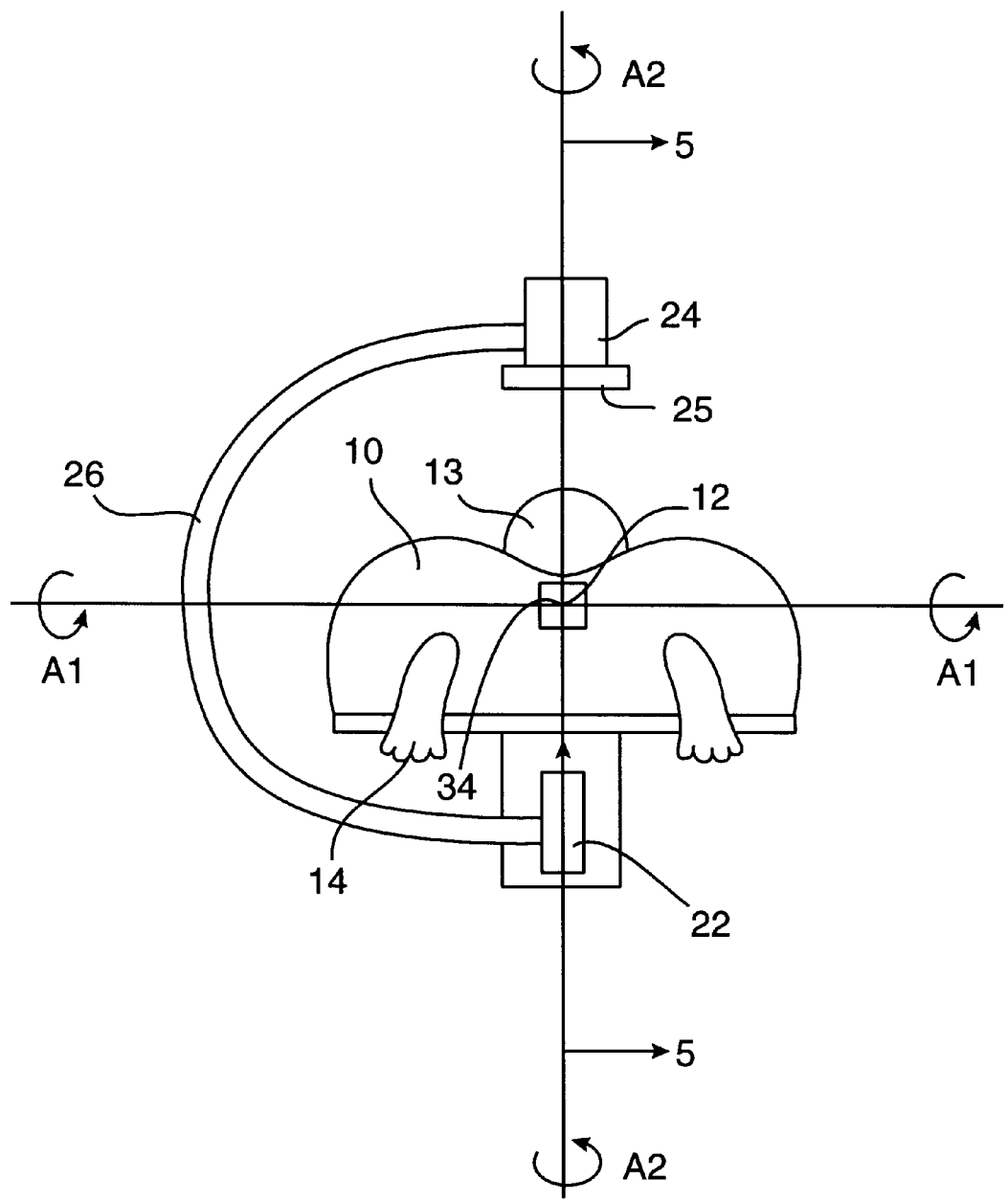
FIG. 2 is a view corresponding to FIG. 1, but with the image intensifier taking an anterior-posterior view through the patient.

Referring first to FIG. 1, a patient 10 having a spine 12, head 13 and feet 14 is positioned in a prone lying manner on a radiotransparent table 15. A conventional image intensifier 20 having an emitter 22 and a receiver 24 which are together held on opposite sides of the patient by a standard C-arm 26 is positioned as shown in FIG. 1 to generate a lateral radioimage view through the patient. As is shown in FIG. 2, C-arm 26 can also be rotated so as to provide an anterior-posterior image through the patient.

C-arm image intensifier 20 may comprise any standard image intensifier, preferably having the property that rotation 24 of C-arm 26 in the plane of the C-arm, (such as from the orientation in FIG. 1 to that of FIG. 2), causes the image intensifier to rotate about a fixed point in space equidistant between emitter 22 and a receiver 24.

In a preferred aspect of the present invention, C-arm 26 is aligned to rotate in a preferred plane about a desired point in space positioned equidistant between emitter 22 and a receiver 24.

In an exemplary aspect of the invention, the desired point in space is disposed within the patient's intervertebral space and the desired plane is an intervertebral plane which passes between adjacent vertebrae, as follows.

Figure 5:
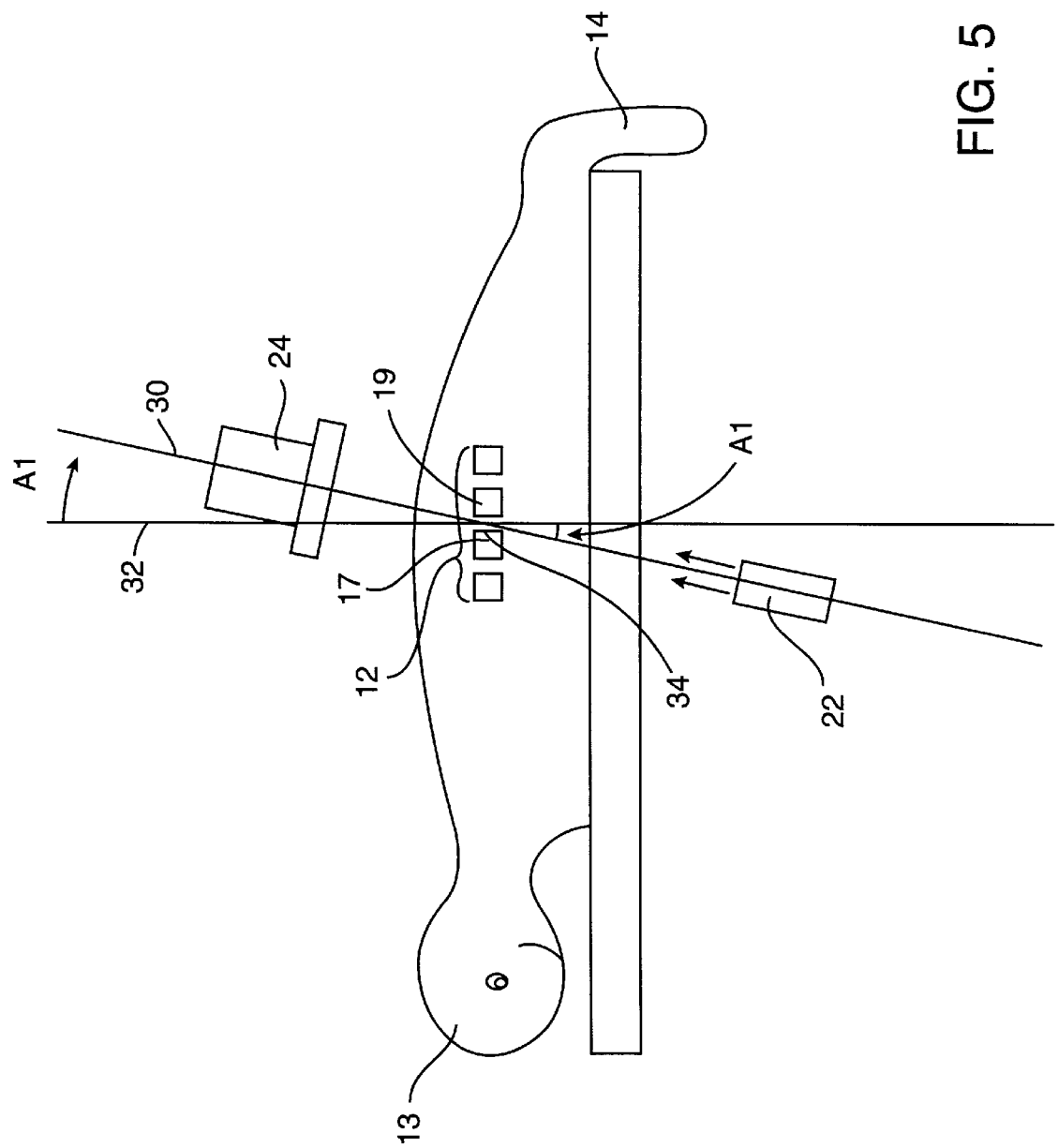
FIG. 5 is a sectional side elevation view taken along line 5—5 in FIG. 2.

When taking either lateral or an anterior-posterior images of adjacent vertebrae in the patient's spine, as seen in FIGS. 1 and 2, respectively, it is preferred to take such images along a plane which passes between the adjacent vertebrae. However, each pair of adjacent vertebrae in the patient's spine will have a different intervertebral plane due to the natural lordosis in the patient's spine. For example, as is seen in FIG. 5, spine 12 comprises adjacent vertebrae 17 and 19. Each pair of adjacent vertebrae in the spine will each have a unique intervertebral plane passing therethrough. For example, intervertebral plane 30 will pass between vertebrae 17 and 19, as shown. Accordingly, considerable adjustment of the image intensifier orientation is required to align it with the selected intervertebral plane. These alignment problems are further complicated when attempting to rotate the image intensifier from a lateral position to an anterior-posterior position.

In a preferred aspect, the present invention may be used to align C-arm 26 image intensifier 20 with intervertebral plane 30 such that as the image intensifier is moved from the position shown in FIG. 1 to the position shown in FIG. 2, C-arm 26 of image intensifier 20 remains at all times disposed in the intervertebral plane 30, as follows.

Figure 3:
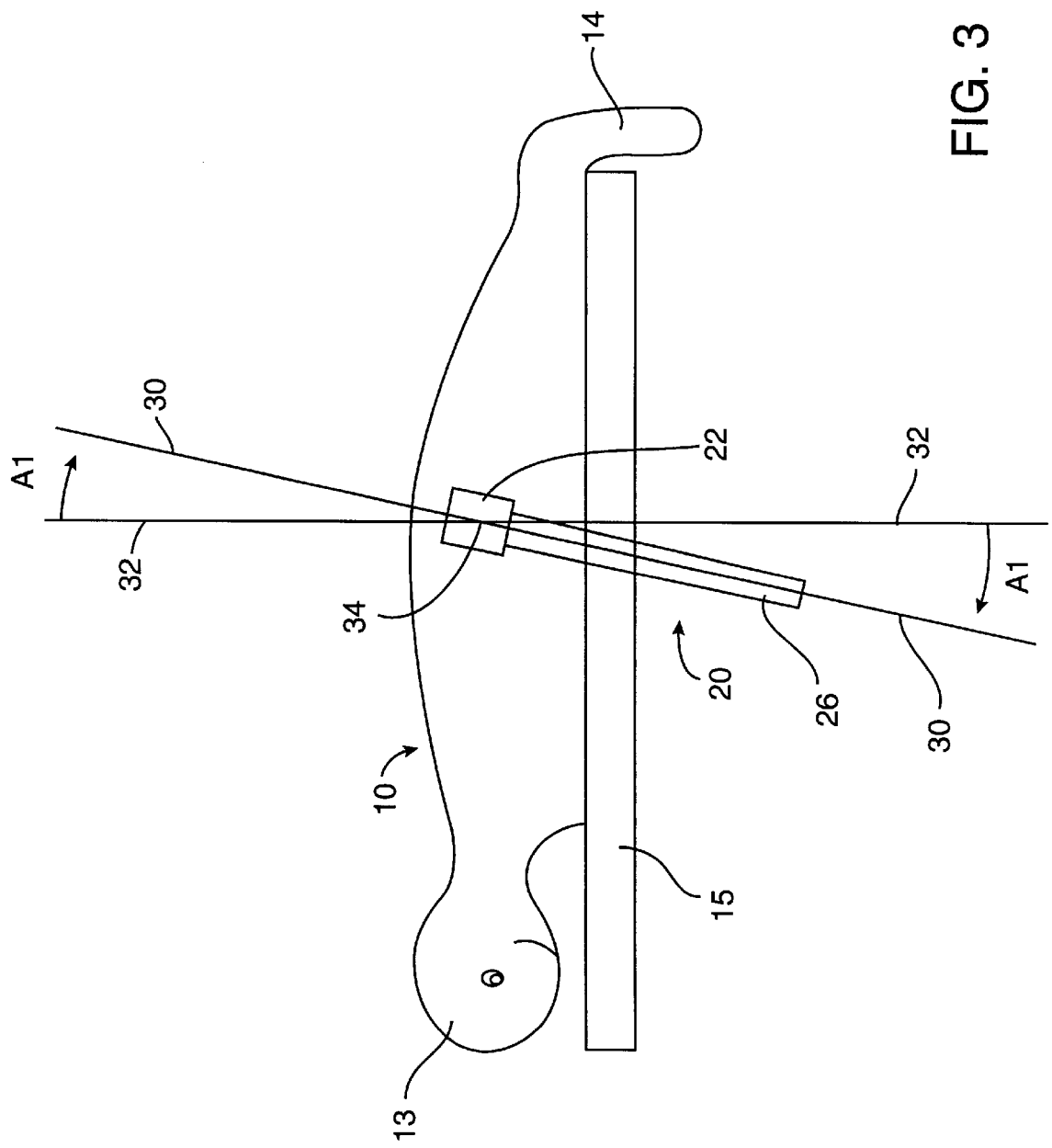
FIG. 3 is a side elevation view corresponding to FIG. 1.
Figure 4:
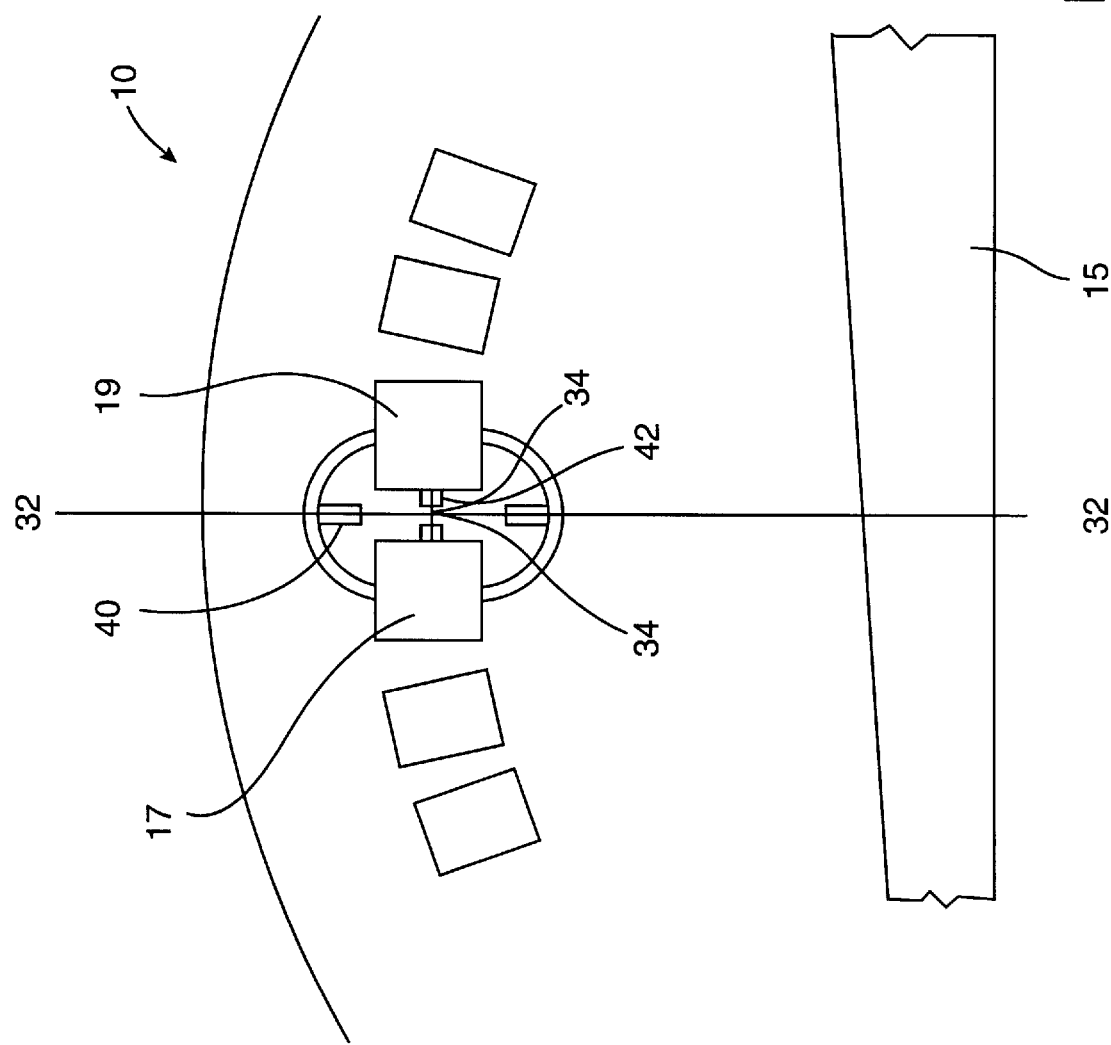
FIG. 4 is a view of an image taken by the image intensifier with the image intensifier being positioned as shown in FIGS. 1 and 3.

As can be seen in FIGS. 3 and 5, the positioning of the image intensifier 20 to align C-arm 26 with a selected intervertebral plane 30 will require C-arm 26 to be rotated by angle Al to a vertical plane 32. The point 34 about which image intensifier 20 is pivoted should preferably be between adjacent vertebrae 17 and 19, (as determined by viewing the lateral image through the patient as shown in FIG. 4 as will be explained). Image intensifier 20 is preferably initially positioned about the patient such that point 34 will be disposed equidistant between emitter 22 and a receiver 24. Accordingly, rotation of C-arm 26 in plane 30 will be about point 34 with point 34 remaining equidistant between emitter 22 and a receiver 24. The correct angling of C-arm 26 about point 34 is accomplished as follows.

Figure 7:
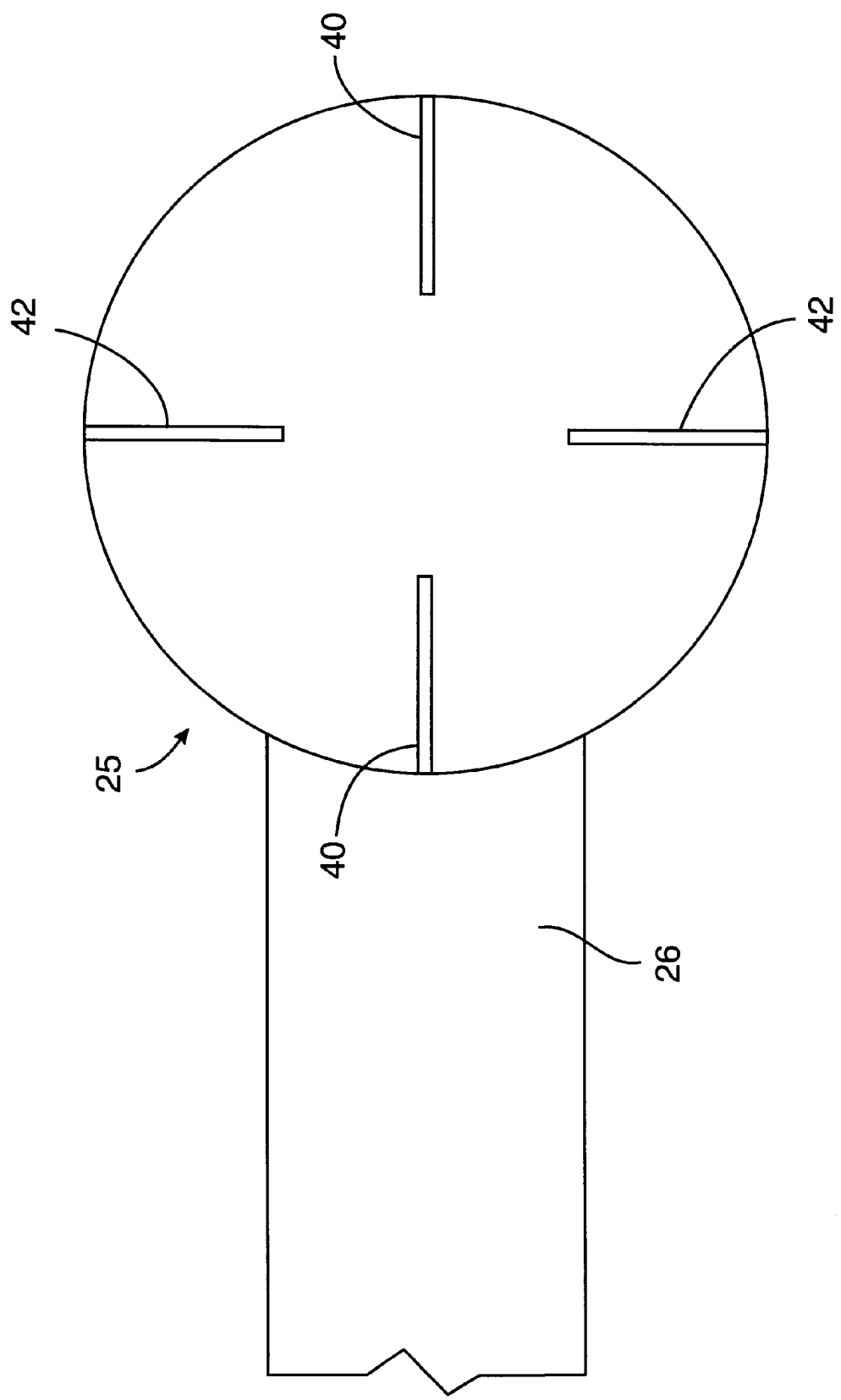
FIG. 7 is an end view of a reticle of the present invention as attached over the receiving end of the image intensifier.

As is seen in FIG. 4, when the image intensifier is positioned as shown in FIGS. 1 and 3, images of adjacent vertebrae 17 and 19 will be seen. Receiver 24 is covered with reticle 25 which has radiopaque indicia, for example, crosshairs 40 and 42 as shown in FIG. 7. Being radiopaque, crosshairs 40 and 42 will also appear on the image viewed by the system operator.

Adjusting the vertical and horizontal position of C-arm 26 of image intensifier 20 will enable the image of the intersection point of crosshairs 40 and 42 to be positioned between adjacent vertebrae 17 and 19 collinear with point 34 when the C-arm is positioned to take a lateral view as illustrated in FIGS. 1 and 4.

Figure 6:
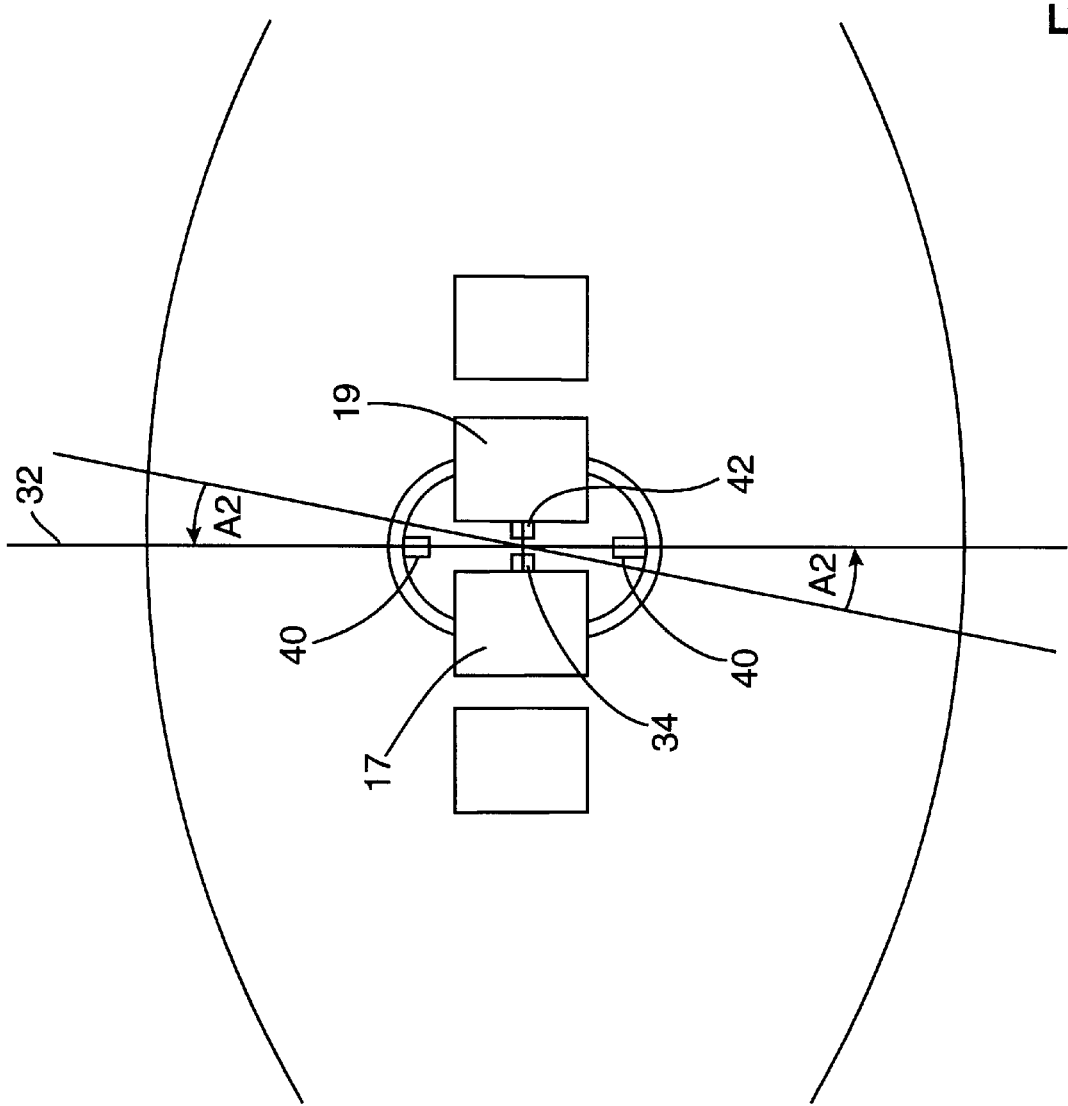
FIG. 6 is a view of an image taken by the image intensifier with the image intensifier being positioned as shown in FIGS. 2 and 5.

Similarly, adjusting the vertical and horizontal position of C-arm 26 of image intensifier 20 will enable the image of the intersection point of crosshairs 40 and 42 to be positioned between adjacent vertebrae 17 and 19 collinear with point 34 as shown when the C-arm is positioned to take an anterior-posterior view as illustrated in FIGS. 2 and 6. In order to align C-arm 26 in the anterior-posterior view of FIGS. 2 and 6, C-arm 26 can be rotated by oblique angle A2.

When crosshairs 40 are aligned in the intervertebral plane in both lateral and anterior-posterior images, rotation of C-arm 26 in its plane of rotation (ie: the plane defined by crosshair 40 on reticle 25, about point 34), will align the C-arm for rotation in a plane which is co-planar to the patient's intervertebral plane. Specifically, when reticle 25 is initially attached to receiver 24, crosshairs 40 are pre-aligned to be coplanar with the plane of rotation of C-arm 26 as is shown in FIG. 7.

After aligning radiopaque crosshairs 40 with intervertebral plane 32, the image intensifier can then be rotated to any position in plane 30 about point 34, (which is also viewable as the intersection point of crosshairs 40 and 42), including an anterior-posterior orientation as is shown in FIGS. 3 and 5, thus aligning C-arm 26 of image intensifier 20 with the intervertebral plane 30.

Once positioned as is shown in FIGS. 1 and 3, image intensifier 20 can then be easily rotated into the position shown in FIGS. 2 and 5 with C-arm 26 remaining in plane 30 to take an anterior-posterior image.

It is to be understood that alignment of image intensifier 20 with plane 32 can also be accomplished first with the image intensifier positioned to take an anterior-posterior view. For example, FIG. 6 shows an illustration of the image intensifier view through adjacent vertebrae 17 and 19 taken along intervertebral plane 30 when the image intensifier is positioned in the orientation shown in FIGS. 2 and 5. Subsequently, image intensifier 20 can be easily rotated to take a lateral view while C-arm 26 remains in the selected intervertebral plane 30. Alignment of the image intensifier with the selected intervertebral plane can also be accomplished at positions between lateral and anterior-posterior orientations.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of aligning a C-arm of an image intensifier for rotation in a selected plane, the C-arm having a transmitter mounted at one end and a receiver mounted at an opposite end, comprising:

identifying the selected plane by viewing the location of bony structures with the image intensifier; and aligning indicia disposed on a radio-opaque reticle covering at least a portion the receiver with the selected plane, the reticle being attached to the receiver such that the indicia are pre-aligned with the plane of rotation of the C-arm, thereby aligning the plane of the C-arm with the selected plane.

2. The method of claim 1, further comprising:

rotating the C-arm in the selected plane.

3. The method of claim 1, further comprising:

rotating the C-arm about a selected point in the selected plane.

4. The method of claim 3, wherein the C-arm is positioned such that the selected point is positioned equidistantly between the receiver and the emitter disposed at opposite ends of the C-arm.

5. The method of claim 3, wherein the indicia comprise first indicia disposed in the plane of rotation of the C-arm and second indicia disposed perpendicular to the plane of rotation of the C-arm.

6. The method of claim 5, further comprising:

centering the selected point between the first and second indicia.

7. The method of any of claims 1 to 6, wherein, the selected plane is an intervertebral plane.

8. A system for aligning a C-arm of an image intensifier for rotation in a selected plane, comprising:

a C-arm image intensifier having a transmitter mounted at one end and a receiver mounted at an opposite end; and a reticle covering the receiver, the reticle being mounted to the receiver with first crosshair indicia fixedly disposed in the plane of rotation of the C-arm and second crosshair indicia disposed perpendicular to the selected plane of rotation of the C-arm, wherein the first and second crosshair indicia of the reticle are perpendicular to one another, but do not cross over one another.

* * * * *